United States Patent [19]

Tanaka et al.

[11] Patent Number: 5,801,238

[45] Date of Patent: Sep. 1, 1998

[54] METHOD FOR PRODUCING WATER ABSORBENT RESIN AND WATER ABSORBENT

[75] Inventors: Keiji Tanaka, Kyoto-fu; Masashi Date, Osaka-fu; Kenjiro Tsubota; Tsuyoshi Yuki, both of Kyoto-fu; Satoshi Tamabuchi, Osaka-fu, all of Japan

[73] Assignee: Sanyo Chemical Industries, Ltd., Kyoto-fu, Japan

[21] Appl. No.: 711,544

[22] Filed: Sep. 10, 1996

[30] Foreign Application Priority Data

Sep. 13, 1995 [JP] Japan ................... 7-262098

[51] Int. Cl.$^6$ ............... C07H 1/00; C07H 5/10; B01J 20/00
[52] U.S. Cl. .......... 536/123.1; 536/118; 536/119; 536/126; 526/321; 502/401; 502/402; 502/404
[58] Field of Search ................... 536/123.1, 118, 536/119, 126; 526/321; 502/401, 402, 404

[56] References Cited

U.S. PATENT DOCUMENTS

| | | | |
|---|---|---|---|
| 4,076,663 | 2/1978 | Masuda et al. | 525/54.31 |
| 5,281,683 | 1/1994 | Yano et al. | 526/323.2 |
| 5,314,420 | 5/1994 | Smith et al. | 604/358 |
| 5,474,915 | 12/1995 | Dordick et al. | 536/119 |

FOREIGN PATENT DOCUMENTS

| | | |
|---|---|---|
| A-63-127754 | 5/1963 | Japan. |
| A-63-118375 | 5/1988 | Japan. |
| A-63-152667 | 6/1988 | Japan. |

*Primary Examiner*—John Kight
*Assistant Examiner*—Everett White
*Attorney, Agent, or Firm*—Merchant, Gould, Smith, Edell, Welter & Schmidt, P.A.

[57] ABSTRACT

A method for producing a water absorbent resin comprising the step of radically polymerizing a water-soluble radically polymerizable monomer having an acid group or a group of the salt thereof and optionally a polysaccharide in the presence of water using a crosslinking agent (C), wherein 0.0001 to 1 weight % of a thiol compound (D) having a radically polymerizable double bond, based on the above mentioned water-soluble radically polymerizable monomer (A), is used as the copolymerizing component to provide a water absorbent resin having a high absorbency and a good gel stability after absorbing body fluid, and a water absorbent comprising the water absorbent resin produced thereby.

6 Claims, No Drawings

METHOD FOR PRODUCING WATER ABSORBENT RESIN AND WATER ABSORBENT

BACKGROUND OF THE INVENTION

1. Field of the Invention

The present invention relates to a method for producing water absorbent resins and water absorbents comprising the water absorbent resins. More specifically, it relates to a method for producing water absorbent resins having high absorbency without load and retention and a good gel stability after absorbing body fluid, and water absorbents comprising the water absorbent resins.

2. Description of the Prior Art

Water absorbent resins are increasingly applied to various industrial fields such as hygienic materials including sanitary napkins and disposable diapers, anti-dewing materials, and agricultural or horticultural water retaining materials.

Water absorbent resins used in such applications as water absorbents are required to have high absorbency without load and retention. In particular, hygienic materials are required to have a good stability after absorbing body fluid, that is, to maintain the water retaining state stably without deterioration of the gel after absorption.

Theoretically, the water absorbing ability without load (absorbency without load and retention) of water absorbent resins is, in general, in proportion to "(ion osmotic pressure+ affinity of the polymer chain to water)/crosslinking density of the polymer". That is, the crosslinking density affects the properties of the water absorbent resin.

Accordingly, water absorbent resins are produced by polymerizing water-soluble monomers to an appropriate crosslinking density with a crosslinking agent or a grafting agent. The adjustment of the crosslinking density is controlled by the amount of a crosslinking agent or a grafting agent, the polymerization concentration, polymerization temperature and the kind of polymerization catalysts.

However, although the crosslinking density can be adjusted by optimizing crosslinking density by reducing the amount of the crosslinking agent or by constraining self-crosslinking by adding a chain transfer agent, since the absorbing ability becomes lowered by a high crosslinking density owing to self-crosslinking by the polymerization propagating radicals during polymerization, these methods can not provide sufficient stability of the gel after absorbing body fluids such as urine and blood.

Further, retention ability may decrease by the deterioration of the gel after absorbing body fluid. The cause of the deterioration is not known clearly, but it is considered that some active material included in the body fluid generates radicals, which decomposes the polymer chain. Therefore, although a method of adding a radical scavenger to the water absorbent resin is proposed for the gel stability after body fluid absorption, the method cannot scavenge the radical efficiently and thus the gel deterioration cannot be avoided sufficiently (JP-A-63-152667).

According to the present invention, the above mentioned problems can be rectified by using a water absorbent comprising a water absorbent resin using a thiol compound having a radically polymerizable double bond as the copolymerization component at the time of polymerization.

SUMMARY OF THE INVENTION

It is an object of the present invention to provide a method for producing water absorbents having a high absorbency without load and a good stability of the gel after absorbing body fluid.

It is another object of the present invention to provide water absorbents having a high absorbency without load and a good stability of the gel after absorbing body fluid.

That is, the present invention relates to a method for producing a water absorbent resin comprising radically polymerizing a water soluble radically polymerizable monomer (A) having an acid group or a group of the salt thereof, or the above mentioned (A) and a polysaccharide (B), in the presence of water using a crosslinking agent (C), wherein 0.0001 to 1 weight % of a thiol compound (D) having a radically polymerizable double bond based on the above mentioned water-soluble radically polymerizable monomer (A) is used as a copolymerizing component.

The present invention further relates to a water absorbent obtained by the method for producing a water absorbent resin comprising radically polymerizing a water-soluble radical polymerizable monomer (A) having an acid group or a group of the salt thereof, or the above mentioned (A) and a polysaccharide (B), in the presence of water using a crosslinking agent (C), wherein 0.0001 to 1 weight % of a thiol compound (D) having a radically polymerizable double bond based on the above mentioned water-soluble radically polymerizable monomer (A) is used as a copolymerizing component.

DESCRIPTION OF THE PREFERRED EMBODIMENT

Examples of the water-soluble monomers (A) in the present invention include radically polymerizable water soluble monomers having a carboxylic acid group, a sulfonic acid group or a phosphoric acid group, and salts of these monomers.

Examples of radically polymerizable water soluble monomers having a carboxylic acid group include unsaturated mono- or poly-carboxylic acids (such as (meth)acrylic acid (This term denotes acrylic acid and/or methacrylic acid. The same should be understood hereinafter.), crotonic acid, sorbic acid, maleic acid, itaconic acid and cinnamic acid), and anhydrides of these monomers (such as maleic anhydride).

Examples of radically polymerizable water soluble monomers having a sulfonic acid group include aliphatic or aromatic vinyl sulfonic acids (such as vinyl sulfonic acid, alkyl sulfonic acid, vinyl toluene sulfonic acid and styrene sulfonic acid), (meth)acryl alkyl sulfonic acids having an alkyl group of 2 to 4 carbon atoms (such as sulfoethyl (meth)acrylate and sulfopropyl (meth)acrylate), and (meth) acrylamide alkyl sulfonic acids having an alkyl group of 2 to 4 carbon atoms such as 2-acrylamide-2-methylpropane sulfonic acid.

Examples of radically polymerizable water-soluble monomers having a phosphoric acid group include phosphoric acid monoesters of hydroxy alkyl (meth)acrylate having an alkyl group of 2 to 4 carbon atoms (such as 2-hydroxyethyl (meth)acryloyl phosphate and phenyl-2-acryloyloxy ethylphosphate).

Radically polymerizable water-soluble monomers having these acid groups may be used either alone or in a combination of two or more.

Among these examples, radically polymerizable water-soluble monomers having a carboxylic acid group or a sulfonic acid group are preferable. In particular, radically polymerizable water-soluble monomers having a carboxylic acid group are particularly preferable.

Radically polymerizable water-soluble monomers having an acid group can be used in a form of their water-soluble salts. Examples of such salts include alkaline metal salts (such as salts of sodium, potassium or lithium), alkaline earth metal salts (such as salts of calcium or magnesium), ammonium salts and amine salts (such as salts of alkylamines having 1 to 6 carbon atoms including methyl amine and trimethyl amine, and salts of alkanol amines having 2 to 6 carbon atoms including triethanol amine and diethanol amine), and a combination of two or more of these. Among these examples, sodium salt and potassium salt are preferable.

The neutralization degree of radically polymerizable water-soluble monomers having an acid group (A) is, in general, 50 to 90 mole %, preferably 60 to 80 mole % based on the neutralization degree of the acid group contained in the water absorbent resin. A neutralization degree of 50 mole % or more is preferable since the stickiness of the obtained hydrogel polymer does not become too large, thus enabling the efficient production of the water absorbent resin. Further, a neutralization degree of 90 mole % or less is preferable with respect to safety since the pH of the obtained polymer does not become too high and therefore does not irritate human skin.

This neutralization can be conducted at any stage of the production process for the water absorbent resins, for example, at the stage of radically polymerizable water-soluble monomers (A) or at the stage of a hydrogel as a polymerization product.

Examples of polysaccharides (B) optionally used in this invention include starches and celluloses. Examples of starches include raw starches such as sweet potato starch, potato starch, wheat starch, corn starch and rice starch; and processed starches such as oxidized starch, dialdehyde starch, alkyl etherified starch, allyletherified starch, oxyalkylated starch and aminoethyl etherified starch.

Examples of celluloses include celluloses obtained from lumber, leaves, stalks, basts and seed fibers; and processed celluloses such as alkyl etherified cellulose, organic acid esterified cellulose, oxidized cellulose and hydroxyalkyl etherified cellulose.

The amount of a polysaccharide (B) to a radically-polymerizable water-soluble monomer (A) is, in general, from 0 to 30 weight %, preferably from 3 to 30 weight %, and more preferably from 3 to 20 weight %. If the amount of a polysaccharide exceeds 30 weight %, the absorbing ability of the obtained water absorbent resin can be deteriorated.

Examples of crosslinking agents (C) in the present invention include compounds having at least two polymerizable double bonds (C1) and compounds having at least one polymerizable double bond and at least one functional group reactive with the monomer (C2).

Examples of the above-mentioned crosslinking agents (C1) include the following:

① bis(meth)acrylamide:

N,N'-alkylene bis(meth)acryl amide having an alkylene group of from 1 to 6 carbon atoms, such as N,N'-methylene bisacryl amide.

② di- or poly- (meth)allyl ether of polyols:

di- or poly- (meth)allyl ether of polyols (such as alkylene glycol, glycerol, polyalkylene glycol, polyalkylene polyol and carbohydrate). For example, pentaerythritol triallyl ether, polyethylene glycol diallyl ether, allylated starch and allylated cellulose are included.

③ carbamyl ester:

carbamyl ester obtained by the reaction of hydroxyethyl (meth)acrylate and a polyisocyanate {such as tolylene diisocyanate, hexamethylene diisocyanate, 4,4'-diphenyl methane diisocyanate, and NCO group-containing prepolymers (obtained by the reaction of the above-mentioned polyisocyanates and a compound having an active hydrogen atom)}.

④ di- or poly- vinyl compound:

such as divinyl benzene, divinyl toluene, divinyl xylene, divinyl ether, divinyl ketone and trivinyl benzene.

⑤ di- or poly- ester of polyols and unsaturated mono- or poly-carboxylic acid:

di- or tri- (meth)acrylate of polyols (such as ethylene glycol, trimethylol propane, glycerol, polyoxyethylene glycol and polyoxy propylene glycol);

unsaturated polyesters (obtained by the reaction of the above-mentioned polyols and an unsaturated acid such as maleic acid);

and di- or tri- (meth)acrylate (obtained by the reaction of polyepoxide and (meth)acrylic acid).

⑥ di- or poly- allylester of polycarboxylic acid:

such as diallyl phthalate and diallyl adipate.

⑦ ester of unsaturated mono- or poly- carboxylic acid and mono(meth)allyl ether of polyol:

such as (meth)acrylate of polyethylene glycol monoallyl ether.

⑧ allyloxy alkanes:

such as tetra allyloxy ethane and triallyloxy ethane.

Examples of the crosslinking agents (C2) include ethylenically unsaturated compounds having a group reactive with (meth)acrylic acid and/or other copolymerizable monomers, in other words, an ethylenically unsaturated compound having a group reactive with a group such as a carboxyl group or carboxylic anhydride group, (for example, a hydroxyl group, an epoxy group and a cationic group). Specific examples include unsaturated compounds having a nonionic group including unsaturated compounds having a hydroxy group (such as N-methylol (meth)acrylamide) and unsaturated compounds having an epoxy group (such as glycidyl (meth)acrylate); unsaturated compounds having a cationic group including unsaturated compounds having a quaternary ammonium salt group (such as N,N,N-trimethyl-N-(meth)acryloyloxyethyl trimethyl ammonium chloride, and N,N,N-trimethyl-N-(meth)acryloyloxyethyl ammonium chloride) and unsaturated compounds having a tertiary amino group (such as dimethyl amino ethyl (meth)acrylate and diethyl amino ethyl (meth)acrylate).

The above-mentioned crosslinking agents (C1), (C2) can be used in a combination of two or more.

Among crosslinking agents (C), crosslinking agents (C1) are preferable. In particular, bis(meth)acrylamide, di- or poly-(meth)allyl ether of polyols, di- or poly- ester of polyols with unsaturated monocarboxylic acids and allyloxy alkanes are preferable. Further, N,N'-methylene bisacryl amide, pentaerythritol triallyl ether, ethylene glycol diacrylate, trimethylol propane triacrylate and tetra allyloxy ethane are more preferable.

The amount of the crosslinking agent (C) to the total weight of the water-soluble monomer (A) and the crosslinking agent (C) is, in general, from 0.0001 to 10 weight %, preferably from 0.001 to 5 weight %, more preferably from 0.01 to 2 weight %. It is preferable to have 0.0001 weight % or more of the amount of a crosslinking agent (C) since a resin having a large gel strength at the time of water absorption can be obtained. On the other hand, it is preferable to have 10 weight % or less of a crosslinking agent (C) since deterioration of the absorbing ability of the obtained gel due to excessive gel strength can be prevented.

As thiol compounds (D) having a radically polymerizable double bond in this invention, compounds capable of being copolymerized with (A) and (C) efficiently and dissolved in the polymerizable monomer solution of the radical polymerization are preferable.

Examples of the thiol compounds (D) include (meth)allyl mercaptan (D1) represented by the general formula (1), (meth)acrylic acid thioester having a thiol group at the end (D2) represented by the general formula (2), styrene derivatives containing an SH-group (D3) represented by the general formula (3).

Compounds (D1) are represented by formula (1):

$$CH_2=C(R^1)CH_2SH \qquad (1)$$

wherein: $R^1$ denotes H or $CH_3$.

Compounds (D2) are represented by formula (2):

$$CH_2=C(R^2)\underset{\underset{O}{\|}}{C}X^1(CH(R^3)CH_2X^2)_nCH_2CH_2SH \qquad (2)$$

wherein:

$R^2$ and $R^3$ denote H or $CH_3$;

$X^1$ and $X^2$ denote O or S; and n denotes O or a positive integer from 1 to 10.

Compounds (D3) are represented by formula (3):

$$CH_2=CH-Ph-SH \qquad (3)$$

wherein Ph denotes a phenylene group.

Examples of (D2) include an ethylene sulfide 1 mole adduct of hydroxy ethyl acrylate, an ester of triethylene glycol dimercaptan and acrylic acid, and an ethylene sulfide 2 moles adduct of acrylic acid. Examples of (D3) include p-mercapto styrene.

Among these examples, (D1) and (D2) are preferable. In particular, (D1) is preferable.

The amount of a thiol compound (D) used in the present invention is, in general, from 0.0001 to 1 weight %, preferably from 0.001 to 0.1 weight % based on the weight of (A). It is preferable that the amount is 0.0001 weight % or more because it achieves effects of the present invention sufficiently to obtain a water absorbent having improved absorbing ability and gel stability after absorbing body fluid. Further, it is preferable that the amount is 1 weight % or less because it enables a reduction in self-crosslinking sufficiently and prevents increase of a water-soluble component amount.

As the method of the radical polymerization in the presence of water in the present invention, a conventional method can be used. Examples of such conventional polymerization methods include aqueous solution polymerization, suspension polymerization, and reverse phase suspension polymerization using a radical polymerization catalyst. Further, as a method of initiating polymerization, a method of irradiating a radioactive ray, electron beam or ultraviolet ray can be adopted.

Examples of radical polymerization catalysts in the method using radical polymerization catalysts include azo compounds (such as azobisisobutyronitrile, azobiscyanovaleric acid and 2,2'-azobis(2-amidinopropane)hydrochloride), inorganic peroxides (such as hydrogen peroxide, ammonium persulfate, potassium persulfate and sodium persulfate), organic peroxides (such as benzoyl peroxide, di-t-butyl peroxide, cumene hydro peroxide, succinic peroxide and di(2-ethoxy ethyl)peroxydicarbonate), and redox catalysts (such as those comprising a combination of a reducing agent (including a sulfite or a bisulfite salt of an alkali metal, ammonium sulfite, ammonium bisulfite, ascorbic acid), and an oxidizing agent (including persulfate of an alkali metal, ammonium persulfate, peroxides)), and the combination of two or more of these.

Redox catalysts comprising a combination of hydrogen peroxide and ascorbic acid, or sodium persulfate and sodium bisulfite can be used as well.

The amount of the catalysts is similar to that used in conventional polymerization methods, in general, from 0.0001 to 5 weight %, preferably from 0.0005 to 1 weight % based on the total weight of the polymerizable monomer (A) and the crosslinking agent (C).

Conventional conditions can be applied in terms of other polymerization conditions such as polymerization concentration, polymerization initiating temperature, polymerization time and maturing temperature.

The hydrogel after polymerization can be dried and pulverized by a conventional method. Examples of drying methods include a method of loading the material on porous plates, wire gauzes, flat plates, or belts and drying by each batch or drying continuously, a method of hot-air drying in a rotary kiln or a fluidized drying oven, a method of heat drying by contact with the surface of a hot plate or a hot roller and a method of heat drying with reduced pressure.

The surface of the water absorbent resin particles obtained in the present invention by drying and pulverizing may be further processed by conventional surface crosslinking using a cross linking agent such as a polyglycidyl ether compound, a polyol compound, a polyamide compound or a polyvalent metal compound.

Since water absorbent resins of the present invention obtained as heretofore mentioned reduce self-crosslinking, and achieve an optimum network structure of a polymer chain generated by polymerization of monomers and an optional crosslinking agent or graft agent, they are preferably used as the water absorbents of the present invention and provide high absorbing ability. "Self-crosslinking" denotes the state where polymer chains crosslink to each other in the process of the radical polymerization without using a crosslinking agent. Although the system of the self-crosslinking has not been clarified yet, it is known that a resin crosslinked by the self-crosslinking causes gel deterioration at the time of water absorption and thus the water retention state cannot be maintained. Accordingly, compared with the crosslinking with a crosslinking agent, the self-crosslinking may have a weaker bond and a tendency to deteriorate. Further, water absorbents of the present invention can provide a good gel stability after absorbing body fluid and thus are preferable for the use in hygienic materials since radicals can be scavenged efficiently even when an impurity generates radicals after absorbing body fluid, to avoid polymer decomposition, owing to the existence of SH in the polymer chain of the water absorbent resin.

The present invention will be further explained with reference to Examples and Comparative Examples, however, the present invention is not limited to the embodiments described herein.

The water-solubility of a thiol compound in the polymerizable monomer solution, and the absorbency without load and the gel stability of the water absorbent resin described in the Examples and the Comparative Examples are the values calculated by the following operation.

<Water-solubility of a thiol compound>

0.06 g of a thiol compound was added to 6 g of acrylic acid with stirring, and then mixed with 20 g of water. After leaving for 30 minutes at 5° C., the appearance was visually observed and judged in terms of dissolving, deposition and cloudiness.

<Absorbency without load>

1.00 g of the water absorbent resin exactly measured was placed in a 250 mesh nylon tea bag and immersed in a 0.9 weight % aqueous solution of sodium chloride for one hour. After draining for 15 minutes, the weight (a) g was measured. Also, the same procedure was conducted with the bag not having the sample therein and the weight (b) g was measured. The absorbency without load was calculated from the below-mentioned formula.

Absorbency without load $(g/g)=((a)-(b))-1$

<Gel stability>

40 g of adult human urine was absorbed by 1 g of a water absorbent resin and left at 25° C. for one hour and 24 hours respectively. Then the gel strength was calculated by the stress received by the cell with a creep meter "RE3305" commercially available from Yamaden, Ltd. and the gel stability was sought by the below mentioned formula:

Gel stability $(\%)=100-((C)-(D))\times 100/(C)$ wherein (C) denotes a gel strength after leaving for one hour, and (D) denotes a gel strength after leaving for 24 hours.

EXAMPLE 1

196 g of acrylic acid, 0.6 g of methylenebisacrylamide, 675 g of deionized water, and 0.02 g of allyl mercaptane were mixed and the polymerizable monomer solution was prepared. The mixture liquid was placed in an adiabatic polymerization reactor. By keeping the temperature at 5° C. or lower and introducing nitrogen gas thereto, the dissolved oxygen amount in the solution was reduced to 1 ppm or less. Then 0.03 g of a 35 weight % aqueous solution of hydrogen peroxide, 0.005 g of ascorbic acid, and 0.05 g of the azo catalyst "V-50" commercially available from Wako Pure Chemical Industries, Ltd. were added thereto. After 10 minutes a rise in the temperature to show the initiation of polymerization was observed. After approximately 3 hours the solution reached equilibrium at 65° C. After a 4 hour maturation period, the polymerized hydrogel was obtained.

After pulverizing 600 g of the polymerized hydrogel with a double arm type kneader, 110 g of an aqueous solution of NaOH of 48 weight % concentration was added thereto and further homogenously mixed by means of the double arm type kneader.

The obtained neutralized gel was dried with hot-air at 130° followed by pulverization by means of a mixer for domestic use to a particle size of 20 mesh or smaller, and a water absorbent resin of the present invention was obtained. The solubility of the used thiol compound in the polymerizable monomer solution, the absorbency without load and the gel stability of the water absorbent resin are described in Table 1.

EXAMPLES 2–3

Water absorbent resins of the present invention were obtained using the same conditions as Example 1 except for the kind of each thiol compound added to the polymerizable monomer solution. The solubility of the used thiol compound in the polymerizable monomer solution, the absorbency without load and the gel stability of the water absorbent resin were measured. The results are described in Table 1.

COMPARATIVE EXAMPLE 1

The result of the case when allyl mercaptan was not added in Example 1 is described in Table 1.

COMPARATIVE EXAMPLE 2

The result of the case when 0.02 g of triethylene glycol dimercaptan (TEDM) was added instead of 0.02 g of allyl mercaptan in Example 1 is described in Table 1.

COMPARATIVE EXAMPLE 3

The result of the case when 0.04 g of a compound of ethylene glycol 2 mols adduct of bisphenol A having both ends modified with an SH group (BPES) was added instead of 0.02 g of allyl mercaptan in Example 1 is described in Table 1.

COMPARATIVE EXAMPLE 4

0.5 g of thiourea (TU) was added to 100 g of the water absorbent resin of the Comparative Example 1 and mixed with a blender for 30 minutes to obtain a water absorbent resin. The absorbency without load and the gel stability of the water absorbent resin were measured. The results are described in Table 1.

TABLE 1

| | Thiol compound | | Additive | Absorbency without load (ml/g) | Gel stability (%) |
|---|---|---|---|---|---|
| | kind | solubility | | | |
| Example 1 | D-1 | transparent dissolved | None | 68 | 64 |
| Example 2 | D-2 | transparent dissolved | None | 67 | 61 |
| Example 3 | D-3 | transparent dissolved | None | 66 | 62 |
| Comparative Example 1 | not added | — | None | 54 | 34 |
| Comparative Example 2 | TEDM | transparent dissolved | None | 68 | 40 |
| Comparative Example 3 | BPES | cloudy deposited | None | 53 | 33 |
| Comparative Example 4 | not added | — | TU | 54 | 52 |

In Table 1, abbreviations are used as follows;

D-1: allyl mercaptan

D-2: ester of triethylene glycol dimercaptan and acrylic acid

D-3: P-mercapto styrene

TEDM: triethylene glycol dimercaptan

BPES: a compound of ethylene glycol 2 mols adduct of bisphenol A having both ends modified with an SH group TU: thiourea.

As apparently shown in Table 1, water absorbent resins obtained in the method of the present invention and water absorbents comprising the water absorbent resins have high absorbency and a good gel stability after absorbing body fluid.

Since water absorbents of the present invention have the above-mentioned advantages, they are useful in various industrial applications such as; an application in contact with a human body such as water-absorbing pads and hygienic materials including disposable diapers for infants or adults, sanitary napkins, hygienic cottons, bandages, incontinence pads and paper towels; an application with possibility of contacting foods such as freshness retaining materials for vegetables and fruits or drip absorbing materials for meat or marine products; an application for water retaining materials for plants or soils; and an application for anti-dewing materials for interior materials of construction.

What is claimed is:

1. A method for producing a water absorbent resin comprising radically polymerizing a water-soluble radically polymerizable monomer (A) having an acid group or a group of the salt thereof, or the above mentioned (A) and a polysaccharide (B), in the presence of water using a crosslinking agent (C), wherein 0.0001 to 1 weight % of a thiol compound (D) having a radically polymerizable double bond based on the above mentioned water-soluble radically polymerizable monomer (A) is used as a copolymerizing component, the thiol compound (D) being a compound capable of being dissolved in the monomer solution for the radical polymerization and being a compound represented by a formula selected from the group consisting of the following general formulae (1) to (3);

$$CH_2=C(R^1)CH_2SH \quad (1)$$

wherein: $R^1$ denotes H or $CH_3$;

$$CH_2=C(R^2)CX^1(CH(R^3)CH_2X^2)_nCH_2CH_2SH \quad (2)$$
$$\qquad \quad \| \qquad \qquad \qquad \qquad \qquad$$
$$\qquad \quad O \qquad \qquad \qquad \qquad \qquad$$

wherein:
$R^2$ and $R^3$ denote H or $CH_3$;
$X^1$ and $X^2$ denote O or S; and
n denotes 0 or a positive integer from 1 to 10 and $$CH_2=CH-Ph-SH \quad (3)$$

wherein Ph denotes a phenylene group.

2. The method for producing a water absorbent resin according to claim 1, wherein the amount of the polysaccharide (B) is from 3 to 30 weight % based on the weight of the water-soluble radically polymerizable monomer (A).

3. The method for producing a water absorbent resin according to claim 1, wherein the amount of the crosslinking agent (C) is 0.0001 to 10 weight % based on the total weight of the water-soluble radically polymerizable monomer (A) and the crosslinking agent (C).

4. A water absorbent obtained by radically polymerizing a water-soluble radically polymerizable monomer (A) having an acid group or a group of the salt thereof, or the above mentioned (A) and a polysaccharide (B), in the presence of water using a crosslinking agent (C), wherein 0.0001 to 1 weight % of a thiol compound (D) having a radically polymerizable double bond, based on the above mentioned water-soluble radically polymerizable monomer (A), is used as a copolymerizing component, the thiol compound (D) being a compound capable of being dissolved in the monomer solution for the radical polymerization and being a compound selected from the group consisting of the following general formulae (1) to (3);

$$CH_2=C(R^1)CH_2SH \quad (1)$$

wherein: $R^1$ denotes H or $CH_3$;

$$CH_2=C(R^2)CX^1(CH(R^3)CH_2X^2)_nCH_2CH_2SH \quad (2)$$
$$\qquad \quad \| \qquad \qquad \qquad \qquad \qquad$$
$$\qquad \quad O \qquad \qquad \qquad \qquad \qquad$$

wherein:
$R^2$ and $R^3$ denote H or $CH_3$;
$X^1$ and $X^2$ denote O or S; and
n denotes 0 or a positive integer from 1 to 10; and $$CH_2=CH-Ph-SH \quad (3)$$

wherein Ph denotes a phenylene group.

5. The water absorbent according to claim 4, wherein the amount of the polysaccharide (B) is from 3 to 30 weight % based on the weight of the water-soluble radically polymerizable monomer (A).

6. The water absorbent according to claim 4, wherein the amount of the crosslinking agent (C) is 0.0001 to 10 weight % based on the total weight of the water-soluble radically polymerizable monomer (A) and the crosslinking agent (C).

* * * * *